(12) United States Patent
Ray, II

(10) Patent No.: US 8,895,036 B1
(45) Date of Patent: *Nov. 25, 2014

(54) TOPICAL COMPOSITIONS TO TREAT CIRCULATORY DISORDERS

(71) Applicant: JCDS Holdings, LLC, Conroe, TX (US)

(72) Inventor: Jay Richard Ray, II, Conroe, TX (US)

(73) Assignee: JCDS Holdings, LLC, Conroe, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/195,057

(22) Filed: Mar. 3, 2014

Related U.S. Application Data

(63) Continuation of application No. 13/913,735, filed on Jun. 10, 2013, now Pat. No. 8,663,663.

(51) Int. Cl.
| | | |
|---|---|---|
| *A61K 9/00* | (2006.01) | |
| *A61K 31/52* | (2006.01) | |
| *A61K 31/44* | (2006.01) | |
| *A61K 31/415* | (2006.01) | |
| *A61K 31/24* | (2006.01) | |
| *A61K 31/522* | (2006.01) | |
| *A61K 31/4422* | (2006.01) | |
| *A61K 31/135* | (2006.01) | |
| *A61K 31/195* | (2006.01) | |
| *A61K 31/167* | (2006.01) | |

(52) U.S. Cl.
CPC ............ *A61K 31/522* (2013.01); *A61K 31/4422* (2013.01); *A61K 31/135* (2013.01); *A61K 31/195* (2013.01); *A61K 31/167* (2013.01); *A61K 9/0014* (2013.01)

USPC ...... 424/400; 514/263.22; 514/355; 514/389; 514/537

(58) Field of Classification Search
None
See application file for complete search history.

(56) References Cited

U.S. PATENT DOCUMENTS

| 4,855,300 | A | 8/1989 | Nandi et al. | |
|---|---|---|---|---|
| 7,687,080 | B2 | 3/2010 | Wolicki | |
| 8,663,663 | B1 * | 3/2014 | Ray, II | ............ 424/400 |
| 2004/0101852 | A1 | 5/2004 | Bennett et al. | |
| 2012/0214874 | A1 | 8/2012 | Buyuktimkin | |
| 2012/0270916 | A1 | 10/2012 | Wolicki | |
| 2013/0085171 | A1 | 4/2013 | Ray et al. | |

OTHER PUBLICATIONS

Patent Cooperation Treaty, "International Search Report" U.S. Searching Authority, document of 1 page, Sep. 7, 2014.

* cited by examiner

*Primary Examiner* — Robert A Wax
*Assistant Examiner* — Jeffrey T Palenik
(74) *Attorney, Agent, or Firm* — Akerman LLP

(57) ABSTRACT

The invention relates to transdermal compositions including nifedipine, pentoxifylline, ketamine hydrochloride, gabapentin, lidocaine, and prilocaine that may be used to treat conditions such as circulatory disorders and peripheral neuropathy. Additionally, methods of the invention are directed to treating conditions such as circulatory disorders, peripheral neuropathy, wound healing, blood flow issues, or the like, comprising the steps of transdermal or topical administration of the compositions.

24 Claims, No Drawings

TOPICAL COMPOSITIONS TO TREAT CIRCULATORY DISORDERS

CROSS-REFERENCE TO RELATED APPLICATION

This patent application is a Continuation of U.S. patent application Ser. No. 13/913,735, filed Jun. 10, 2013, the entirety of which is incorporated by reference herein.

FIELD OF INVENTION

The present invention relates to transdermal pharmaceutical compositions containing nifedipine, pentoxifylline, ketamine hydrochloride, gabapentin, lidocaine, and prilocaine that may be used to treat conditions such as circulatory disorders and peripheral neuropathy.

BACKGROUND

A circulatory disorder is any disorder that affects the circulatory system. Circulatory disorders may arise from problems with the heart, blood vessels, or the blood, and may result in diminished blood flow and oxygen supply to the tissues. Common circulatory disorders include hypertension, angina, and arteriosclerosis. People with certain diseases such as diabetes, or kidney failure may be more likely to have circulatory problems.

Peripheral neuropathy is a condition involving nerve-end damage in the body, and it is most often manifested as one or a combination of motor, sensory, sensorimotor, or autonomic neural dysfunctions. Peripheral neuropathy may result from a wide variety of causes. For example, peripheral neuropathies can be genetically acquired, can result from a systemic disease, can manifest as a post-surgical complication, or can be induced by a toxic agent. One common type of neuropathy is diabetic neuropathy which is caused by diabetes.

Specific classes of drugs that may be used for the non-invasive treatment of neuropathy include: (1) non-steroidal anti-inflammatory drugs (NSAIDs); (2) narcotic analgesics; (3) tricyclic antidepressants; and (4) anticonvulsants. Drugs belonging to these classes are available commercially as oral products. However, because drugs belonging to these classes are distributed systemically throughout the body, their various side effects limit their effectiveness. The NSAIDs, for example, when taken orally cause gastric distress including ulcers. The other three classes share other common side effects, including drowsiness, dizziness, disorientation, and gastrointestinal upset.

The present invention is intended to provide pharmaceutical compositions capable of effectively treating conditions such as circulatory disorders and peripheral neuropathy.

SUMMARY

The present invention relates to pharmaceutical compositions containing nifedipine, pentoxifylline, ketamine hydrochloride, gabapentin, lidocaine, and prilocaine, and the use of these compositions to treat conditions such as circulatory disorders and peripheral neuropathy. The pharmaceutical compositions described herein may include any formulations that are suitable for topical application.

In one embodiment a pharmaceutical composition of the invention comprises nifedipine, pentoxifylline, ketamine hydrochloride, gabapentin, lidocaine or pharmaceutically acceptable salts thereof, and prilocaine or pharmaceutically acceptable salts thereof, wherein lidocaine or a pharmaceutically acceptable salt thereof is present in an amount of about 0.1% to about 5%, and prilocaine or a pharmaceutically acceptable salt thereof is present in an amount of about 0.1% to about 5%, and wherein the ratio of nifedipine to pentoxifylline is greater than 1:1.

In another embodiment a pharmaceutical composition of the invention comprises nifedipine in an amount of about 1% to about 25%, pentoxifylline in an amount of about 1% to about 25%, ketamine hydrochloride in an amount of about 5% to about 50%, gabapentin in an amount of about 1% to about 30%, lidocaine or a pharmaceutically acceptable salt thereof in an amount of about 0.1% to about 5%, and prilocaine or a pharmaceutically acceptable salt thereof in an amount of about 0.1% to about 5%.

In a further embodiment a pharmaceutical composition of the invention consists essentially of nifedipine, pentoxifylline, ketamine hydrochloride, gabapentin, lidocaine or a pharmaceutically acceptable salt thereof, prilocaine or a pharmaceutically acceptable salt thereof, and a pharmaceutically acceptable carrier. As used herein, the phrase "consisting essentially of" limits a composition to the specified materials or steps and those additional, undefined components that do not materially affect the basic and novel characteristic(s) of the composition, such as, for example, additional active ingredients.

In an additional embodiment a pharmaceutical composition of the invention consists of nifedipine in an amount of about 10%, pentoxifylline in an amount of about 5%, ketamine hydrochloride in an amount of about 10%, gabapentin in an amount of about 6%, lidocaine hydrochloride monohydrate in an amount of about 3.7%, prilocaine hydrochloride in an amount of about 3.5%, vitamin E acetate in an amount of about 1%, sodium metabisulfite in an amount of about 0.5%, butylated hydroxytoluene in an amount of about 0.05%, and a pharmaceutically acceptable carrier in an amount of about 60.7%. "Consisting of" refers to the inclusion of exactly one element of a number or list of elements.

The invention also encompasses methods for treating circulatory disorders and peripheral neuropathy comprising administering to a patient in need thereof a pharmaceutical composition of the invention.

DETAILED DESCRIPTION OF THE INVENTION

The present invention is directed to pharmaceutical compositions comprising nifedipine, pentoxifylline, ketamine hydrochloride, gabapentin, lidocaine, and prilocaine that are useful for treating conditions such as circulatory disorders and peripheral neuropathy.

In one embodiment, the pharmaceutical composition of the invention may include a therapeutically effective amount of nifedipine, pentoxifylline, ketamine hydrochloride, gabapentin, lidocaine or a pharmaceutically acceptable salt thereof present in an amount of about 0.1% to about 5%, and prilocaine or a pharmaceutically acceptable salt thereof present in an amount of about 0.1% to about 5%, wherein the ratio of nifedipine to pentoxifylline is greater than 1:1.

In a further embodiment, the pharmaceutical composition of the invention may comprise nifedipine in an amount of about 1% to about 25%, about 5% to about 15%, or about 7% to a about 12%; pentoxifylline in an amount of about 1% to about 25%, about 2% to about 15%, or about 3% to about 10%; ketamine hydrochloride in an amount of about 5% to about 50%, about 5% to about 30%, or about 5% to about 10%; gabapentin in an amount of about 1% to about 30%, about 3% to about 15%, or about 5% to about 10%; lidocaine or a pharmaceutically acceptable salt thereof in an amount of about 0.1% to about 5%; and prilocaine or a pharmaceutically acceptable salt thereof in an amount of about 0.1% to about 5%; wherein the ratio of nifedipine to pentoxifylline is greater than 1:1.

In an additional embodiment, the pharmaceutical composition of the invention may consist essentially of nifedipine, pentoxifylline, ketamine hydrochloride, gabapentin, lidocaine or a pharmaceutically acceptable salt thereof, prilocaine or a pharmaceutically acceptable salt thereof, and a pharmaceutically acceptable carrier. In still another embodiment, the pharmaceutical composition of the invention may consist of nifedipine in an amount of about 10%; pentoxifylline in an amount of about 5%; ketamine hydrochloride in an amount of about 10%; gabapentin in an amount of about 6%; lidocaine hydrochloride monohydrate in an amount of about 3.7%; prilocaine hydrochloride in an amount of about 3.5%; vitamin E acetate in an amount of about 1%; sodium metabisulfite in an amount of about 0.5%; butylated hydroxytoluene in an amount of about 0.05%; and a pharmaceutically acceptable carrier in an amount of about 60.7%.

In certain embodiments, the compositions of the invention do not contain clonidine.

Nifedipine is a non-NMDA calcium channel antagonist. Nifedipine has been shown to have an additive protective effect in blocking glutamate insult when combined with ketamine. Nifedipine is useful for treating diabetic peripheral neuropathy and for the treatment of coronary heart diseases and high blood pressure. Nifedipine may be present in the compositions of the invention in concentrations ranging from about 1% to about 25%, for example, from about 5% to about 15% and from about 8% to about 12%. Alternatively, nifedipine may be present in the compositions of the invention in concentrations ranging from 1% to 25%, for example, from 5% to 15% and from 8% to 12%. Nifedipine may also be present in the compositions of the invention in or about the following amounts: 1%, 2%, 3%, 4%, 5%, 6%, 7%, 8%, 9%, 10% 11%, 12%, 13%, 14%, 15%, 16%, 17%, 18%, 19%, 20%, 21%, 22%, 23%, 24%, and 25%. In one embodiment, nifedipine may be present in an amount of or about 10%.

Pentoxifylline is a TNF-a antagonist that is generally used in the treatment of peripheral and cerebral circulation. Pentoxifylline may be present in the compositions of the invention in concentrations ranging from about 1% to about 25%, for example, from about 1% to about 15%, about 1% to about 10%, and about 3% to about 7%. Alternatively, pentoxifylline may be present in the compositions of the invention in concentrations ranging from 1% to 25%, for example, from 1% to 15%, 1% to 10%, and 3% to 7%. Pentoxifylline may also be present in the compositions of the invention in or about the following amounts: 1%, 2%, 3%, 4%, 5%, 6%, 7%, 8%, 9%, 10% 11%, 12%, 13%, 14%, 15%, 16%, 17%, 18%, 19%, 20%, 21%, 22%, 23%, 24%, and 25%. In one embodiment pentoxifylline may be present in the compositions of the invention in an amount of or about 5%. In a further embodiment, the ratio of nifedipine to pentoxifylline in the compositions of the invention may be greater than 2:1.

Ketamine hydrochloride is an N-methyl-D-aspartate (NMDA) calcium channel antagonist. Ketamine hydrochloride may be present in the compositions of the invention in concentrations ranging from about 5% to about 50%, for example, from about 5% to about 30%, about 5% to about 20% about 5% to about 15%, and about 8% to about 12%. Alternatively, ketamine hydrochloride may be present in the compositions described herein in concentrations ranging from 5% to 50%, for example, from 5% to 30%, 5% to 20%, 5% to 15%, and 8% to 12%. Ketamine hydrochloride may also be present in the compositions of the invention in or about the following amounts: 5%, 6%, 7%, 8%, 9%, 10% 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, and 50%. In one embodiment ketamine hydrochloride may be present in an amount of or about 10%.

Gabapentin is a glutamate antagonist at the NMDA and AMPA (sodium channel) receptor sites. Gabapentin may be present in the compositions described herein in concentrations ranging from about 1% to about 30%, for example, from about 1% to about 15%, about 1% to about 10%, and about 4% to about 8%. Alternatively, gabapentin may be present in the compositions of the invention in concentrations ranging from 1% to 30%, for example, from 1% to 15%, 1% to 10%, and 4% to 8%. Gabapentin may also be present in the compositions of the invention in or about the following amounts: 1%, 2%, 3%, 4%, 5%, 6%, 7%, 8%, 9%, 10% 11%, 12%, 13%, 14%, 15%, 16%, 17%, 18%, 19%, 20%, 21%, 22%, 23%, 24%, 25%, 26%, 27%, 28%, 29%, and 30%. In one embodiment gabapentin may be present in an amount of or about 6%.

Lidocaine is a local anesthetic. Lidocaine or a pharmaceutically acceptable salt thereof may be present the compositions of the invention in concentrations ranging from about 0.1% to about 5%, for example, from about 1% to about 5%, about 2% to about 5%, about 3% to about 4%, and about 3% to about 5%. Alternatively, lidocaine or a pharmaceutically acceptable salt thereof may be present in the compositions of the invention in concentrations ranging from 0.1% to 5%, for example, 1% to 5%, 2% to 5%, 3% to 4%, and 3% to 5%. Lidocaine or a pharmaceutically acceptable salt thereof may also be present in the compositions of the invention in or about the following amounts: 0.1%, 1%, 2%, 3%, 4%, and 5%. In one embodiment, lidocaine is lidocaine hydrochloride monohydrate. In a further embodiment lidocaine hydrochloride monohydrate may be present in an amount of or about 3.7%.

Prilocalne is also a local anesthetic. Prilocalne or a pharmaceutically acceptable salt thereof may be present in the compositions of the invention in concentrations ranging from about 0.1% to about 5%, for example, from about 1% to about 5%, about 2% to about 5%, about 3% to about 4%, about 3% to about 5%. Alternatively, prilocaine or a pharmaceutically acceptable salt thereof may be present in the compositions in concentrations ranging from 0.1% to 5%, for example, 1% to 5%, 2% to 5%, 3% to 4%, and 3% to 5%. Prilocalne or a pharmaceutically acceptable salt thereof may also be present in the compositions of the invention in or about the following amounts: 0.1%, 1%, 2%, 3%, 4%, and 5%. In one embodiment prilocaine is prilocaine hydrochloride. In an additional embodiment prilocaine hydrochloride may be present in an amount of or about 3.5%.

The compositions of the invention may further comprise additional ingredients. Additional ingredients may include pharmaceutically acceptable carriers, moisturizers, oils, fats, waxes, surfactants, thickening agents, antioxidants, viscosity stabilizers, chelating agents, buffers, preservatives, perfumes, dyestuffs, lower alkanols, humectants, emollients, dispersants, sunscreens such as radiation blocking compounds or UV-blockers, antibacterials, antifungals, disinfectants, vitamins, antibiotics, anti-acne agents, as well as other suitable materials that do not have a significant adverse effect on the activity of the topical composition. For example, a composition of the invention may comprise the following additional ingredients: vitamin E acetate in an amount of or about 1%, sodium metabisulfite in an amount of or about 0.5%, and butylated hydroxytoluene in an amount of or about 0.05%. Those skilled in the art will readily recognize additional ingredients that may be included in the compositions described herein.

Exemplary pharmaceutical acceptable carriers that may be used in the compositions of the invention may include water, mixtures of water and water-miscible solvents such as lower alkanols or vegetable oils, and water-soluble ophthalmologically acceptable non-toxic polymers (for example, cellulose derivatives such as methylcellulose), glycerin, propylene glycol, methylparaben, alginates, glyceryl stearate, PEG-100 stearate, cetyl alcohol, propylparaben, butylparaben, sorbitols, polyethoxylated anhydrosorbitol monostearate (TWEEN), white petrolatum (VASELINE), triethanolamine, emu oil, aloe vera extract, lanolin, cocoa butter, Lipoderm® base, Lipoderm® ActiveMax base, and the like. The pharmaceutically acceptable carrier may be present in the compositions of the invention in concentrations ranging from about 55% to about 65% or in concentrations ranging from 55% to 65%. For example, the pharmaceutically acceptable carrier may be present in an amount of or about 60.7%. In one embodiment the pharmaceutically acceptable carrier may be Lipoderm® ActiveMax base. In still another embodiment the pharmaceutically acceptable carrier may be Lipoderm® ActiveMax base and it may be present in the compositions of the invention in an amount of or about 60.7%. Table I below lists the base ingredients for the preferred embodiment of the base composition disclosed herein. Other ingredient lists with additional, fewer, or alternate ingredients may be used.

TABLE I

Base Lipoderm ® ActiveMax ™ Ingredients

Water
Cetearyl Alcohol
Plukenetia Volubilis Seed Oil
Isopropyl Myristate
Propylheptyl Caprylate
Sodium Stearoyl Glutamate
PEG-8/SMDI Copolymer
PEG-100 Stearate
Glyceryl Stearate
Glycerin
Tocopheryl Acetate
Lecithin
Hydrogenated Lecithin
Populus Tremuloides Bark Extract
Lonicera Japonica (Honeysuckle) Flower Extract
Lonicera Caprifolium (Honeysuckle) Flower Extract
Leuconostoc/Radish Root Ferment Filtrate
Pentaclethra Macroloba Seed Oil
Butyrospermum Parkii (Shea) Butter
Carthamus Tinctorius (Safflower) Seed Oil
Cocos Nucifera (Coconut) Oil
Tocopherol
Ascorbyl Palmitate
Squalane
Ceramide 3
Alcohol
Glyceryl Stearate
Caprylic/Capric Triglyceride
Xanthan Gum
Gluconolactone
Sodium Dehydroacetate
Disodium EDTA
BHT Pharmaceutical compositions of the invention may be formulated as a topical composition for transdermal delivery. As used herein, "transdermal" delivery relates to delivery of a drug by passage into and through the skin or mucosal tissue. The terms "transdermal", "topical", and "transmucosal" are used interchangeably unless specifically stated otherwise. Exemplary dosage forms include creams, lotions, gels, oils, or ointments, or any other topical forms known to those skilled in the art.

The compositions described herein may be made by cold compounding. This is significant because one or more of the compounds admixed in the compositions described herein may be sensitive to heat or other types of energy. The compositions of the invention may be prepared by mixing the ingredients together without heating and using a sufficient amount of the carrier to provide a substantially homogeneous cream or ointment. The compositions of the invention may be prepared in, for example, a 60 gram, 90 gram, or 120 gram quantity.

Additionally, methods of the invention are directed to treating conditions such as circulatory disorders, peripheral neuropathy, wound healing, blood flow issues, or the like, comprising the steps of transdermal or topical administration of a pharmaceutical composition to a patient in need thereof wherein the pharmaceutical composition contains nifedipine, pentoxifylline, ketamine hydrochloride, gabapentin, lidocaine, and prilocaine. For example, the pharmaceutical composition may comprise nifedipine in an amount of about 1% to about 25%; pentoxifylline in an amount of about 1% to about 25%; ketamine hydrochloride in an amount of about 5% to about 50%; gabapentin in an amount of about 1% to about 30%; lidocaine or a pharmaceutically acceptable salt thereof in an amount of about 0.1% to about 5%, and prilocaine or a pharmaceutically acceptable salt thereof in an amount of about 0.1% to about 5%.

Circulatory disorders may include but are not limited to the following: hypertension, angina, arteriosclerosis, stroke, coronary artery disease, aortic aneurysm, deep vein thrombosis, arteriovenous malformations, and peripheral vascular disease.

The methods and pharmaceutical compositions of the invention may be effective in treating circulatory disorders associated with the following diseases: transitory ischemic attacks, prolonged reversible ischemic neurological deficits, cerebral organic psychosyndrome, coronary heart disease, angina pectoris, hypertension, intermittent claudication, ulcus cruris, gangrene, necrosis resulting in amputation, and Raynard's disease. In some cases, the compositions may be effective to avoid amputation that results from or is a complication of a circulatory disorder or other disorder described herein. Accordingly methods for avoiding amputation by administration of the compositions described herein are contemplated.

The methods and pharmaceutical compositions of the invention may also be used to treat circulatory disorders caused by, for example, trauma, aneurysms, vascular malformations, and Raynaud's disease among others.

Peripheral neuropathies may include but are not limited to the following: diabetic neuropathy, HIV associated neuropathy, $B_{12}$-deficiency associated neuropathy, cranial nerve palsies, drug-induced neuropathy, industrial neuropathy, lymphomatous neuropathy, myelomatous neuropathy, multifocal motor neuropathy, chronic idiopathic sensory neuropathy, carcinomatous neuropathy, acute pan autonomic neuropathy, alcoholic neuropathy, compressive neuropathy, vasculitic/ischaemic neuropathy, and mono- and poly-neuropathies.

Additionally, genetically acquired neuropathies suitable for treatment by the methods and pharmaceutical compositions of the invention may include: peroneal muscular atrophy (Charcot-Marie-Tooth Disease) hereditary amyloid neuropathies, hereditary sensory neuropathy (type I and type II), porphyric neuropathy, hereditary liability to pressure palsy, Fabry's Disease, adrenomyeloneuropathy, Riley-Day Syndrome, Dejerine-Sottas neuropathy (hereditary motor-sensory neuropathy-III), Refsum's disease, ataxia-telangiectasia, hereditary tyrosinemia, anaphalipoproteinemia, abetalipoproteinemia, giant axonal neuropathy, metachromatic leukodystrophy, globoid cell leukodystrophy, and Friedrich's ataxia.

The methods and pharmaceutical compositions of the invention may also be effective in treating neuropathies associated with systemic diseases including but not limited to the following: uremia; childhood cholestatic liver disease; chronic respiratory insufficiency; alcoholic polyneuropathy; multiple organ failure; sepsis; hypo-albuminemia; eosinophilia-myalgia syndrome; hepatitis; porphyria; hypo-glycemia; vitamin deficiency; chronic liver disease; primary biliary cirrhosis; hyperlipidemia; leprosy; Lyme disease; herpes zoster; Guillain-Barre syndrome; chronic inflammatory demyelinating polyradiculoneuropathy; sensory perineuritis; acquired immunodeficiency syndrome (AIDS) associated neuropathy; Sjogren's syndrome; primary vasculitis (such as polyarteritis nodosa); allergic granulomatous angiitis; hypersensitivity angiitis; Wegener's granulomatosis; rheumatoid arthritis; systemic lupus erythematosis; mixed connective tissue disease; scleroderma; sarcoidosis; vasculitis; systemic vasculitides; acute tunnel syndrome; pandysautonomia; primary, secondary, localized or familial systemic amyloidosis; hypothyroidism; chronic obstructive pulmonary disease; acromegaly; malabsorption (sprue, celiac disease); carcinomas (sensory, sensorimotor, late and demyelinating); lymphoma (including Hodgkin's), polycythemia vera; multiple myeloma (lytic type, osteo sclerotic, or solitary plasmacytoma); benign monoclonal gammopathy; macroglobulinemia; cryoglobulinemia; tropical myeloneuropathies; herpes simplex infection; cytomegalovirus infection; and diabetes.

In further embodiments the pharmaceutical compositions of the invention may be used to treat neuropathic pain, especially pain caused by nerve injury or sympathetically mediated pain. Neuropathic pain syndromes include, without limitation, allodynia, various neuralgias such as post herpetic neuralgia and trigeminal neuralgia, phantom limb pain, hyperpathia, hyperesthesia, hyperalgesia, dyesthesia, paresthesia, anesthesia delorosa, deafferentation pain, and complex regional pain syndromes, such as reflex sympathetic dystrophy and causalgia.

In additional embodiments, pharmaceutical compositions of the invention may be used to treat peripheral neuropathy that is caused by an infectious disease, a post-surgical complication, a toxic agent, lower back pain, Guillain-Barre Syndrome, or sciatica.

Methods described herein may also involve the topical application of a pharmaceutical composition of the invention to areas of the skin in the vicinity of tissue that may suffer from neuropathic pain. For example, the pharmaceutical compositions and methods of the invention may be used on a patient's extremities such as the peripheral appendages (e.g., fingers, toes, hands and feet) or in general areas (e.g., back, shoulder, neck) where a patient is experiencing pain. Additionally, the methods and pharmaceutical compositions of the invention may be applied to the specific ganglia that mediate pain to the spinal column and to the spine itself.

The compositions described herein may provide relief of pain, burning, tingling, numbness, electrical sensations, and hyperalgesia to a patient when topically applied in an effective amount. Additionally, the compositions of the invention may provide increased microcirculation, nitric oxide stabilization, and facilitated healing of skin ulcers and lesions, protein kinase C inhibition, decreased oxidative stress, anti-inflammation, protection against radiation damage (particularly ultraviolet radiation), blockage of the formation of leukotrienes, stabilization of cell membranes, and/or promotion of the synthesis of nerve growth factor to a patient when topically applied in an effective amount.

Pharmaceutical compositions of the invention may be topically administered in up to 4 gram doses and may be applied one to three times daily. A sufficient amount of the composition may be applied to cover the afflicted area and may be rubbed in until little or no residue remains on the skin. Any excess residue may be removed. Heat may be applied to the afflicted area both before and after the pharmaceutical composition is topically applied to the afflicted area.

An exemplary 4 gram dose of a pharmaceutical composition of the invention may comprise 0.4 grams nifedipine; 0.2 grams pentoxifylline; 0.4 grams ketamine hydrochloride; 0.24 grams gabapentin; 0.15 grams lidocaine hydrochloride monohydrate; 0.14 grams prilocaine hydrochloride; 0.04 grams vitamin E acetate; 0.002 grams sodium metabisulfite; 0.002 grams butylated hydroxytoluene; and 2.43 grams Lipoderm® ActiveMax base.

The compositions described herein exhibit excellent storage characteristics. The dry formulations described herein are stable for at least about 6 months, or about 180 days from the date of compounding. In some embodiments, the compositions are stable for about 8 months. By "stable," it is meant that each ingredient in the composition retains at least 90% potency over the stated time period.

Certain preferred features are provided by the following numbered clauses:

1. A pharmaceutical composition comprising nifedipine, pentoxifylline, ketamine hydrochloride, gabapentin, lidocaine or pharmaceutically acceptable salt thereof, and prilocaine or pharmaceutically acceptable salts thereof,
   wherein lidocaine or a pharmaceutically acceptable salt thereof is present in an amount of about 0.1% to about 5%, and
   wherein prilocaine or a pharmaceutically acceptable salt thereof is present in an amount of about 0.1% to about 5%, and
   wherein the ratio of nifedipine to pentoxifylline is ≥1:1.

2. The pharmaceutical composition of clause 1, wherein the ratio of nifedipine to pentoxifylline is ≥2:1.

3. The pharmaceutical composition of clause 1, wherein the composition does not contain clonidine.

4. The pharmaceutical composition of clause 1, wherein the composition is formulated as a topical composition.

5. The pharmaceutical composition of clause 1, wherein the composition is incorporated into a formulation selected from the group consisting of: cream, lotion, gel, oil, and ointment.

6. The pharmaceutical composition of clause 1, wherein the composition is in a 60 gram, 90 gram, or 120 gram quantity.

7. The pharmaceutical composition of clause 1, wherein the composition is formulated in up to a 4 gram dose.

8. The pharmaceutical composition of clause 1, wherein the composition is formulated in a pharmaceutically acceptable carrier.

9. The pharmaceutical composition of clause 8, wherein the pharmaceutically acceptable carrier is present in an amount of about 55% to about 65%.

10. The pharmaceutical composition of clause 1, wherein nifedipine is present in an amount of about 1% to about 25%.

11. The pharmaceutical composition of clause 1, wherein nifedipine is present in an amount of about 5% to about 15%.

12. The pharmaceutical composition of clause 1, wherein nifedipine is present in an amount of about 10%.

13. The pharmaceutical composition of clause 1, wherein pentoxifylline is present in an amount of about 1% to about 25%.

14. The pharmaceutical composition of clause 1, wherein pentoxifylline is present in an amount of about 1% to about 10%.

15. The pharmaceutical composition of clause 1, wherein pentoxifylline is present in an amount of about 5%.

16. The pharmaceutical composition of clause 1, wherein ketamine hydrochloride is present in an amount of about 5% to about 50%.

17. The pharmaceutical composition of clause 1, wherein ketamine hydrochloride is present in an amount of about 5% to about 15%.

18. The pharmaceutical composition of clause 1, wherein ketamine hydrochloride is present in an amount of about 10%.

19. The pharmaceutical composition of clause 1, wherein gabapentin is present in an amount of about 1% to about 30%.

20. The pharmaceutical composition of clause 1, wherein gabapentin is present in an amount of about 1% to about 10%.

21. The pharmaceutical composition of clause 1, wherein gabapentin is present in an amount of about 6%.

22. The pharmaceutical composition of clause 1, wherein the lidocaine is lidocaine hydrochloride monohydrate and is present in an amount of about 3.7%.

23. The pharmaceutical composition of clause 1, wherein the prilocaine is prilocaine hydrochloride and is present in an amount of about 3.5%.

24. A pharmaceutical composition comprising:
   a) nifedipine in an amount of about 1% to about 25%;
   b) pentoxifylline in an amount of about 1% to about 25%;
   c) ketamine hydrochloride in an amount of about 5% to about 50%;
   d) gabapentin in an amount of about 1% to about 30%;
   e) lidocaine or a pharmaceutically acceptable salt thereof in an amount of about 0.1% to about 5%; and
   f) prilocaine or a pharmaceutically acceptable salt thereof in an amount of about 0.1% to about 5%;
   wherein the ratio of nifedipine to pentoxifylline is ≥1:1

25. The pharmaceutical composition of clause 24, wherein the ratio of nifedipine to pentoxifylline is ≥2:1.

26. The pharmaceutical composition of clause 24, wherein the composition does not contain clonidine.

27. The pharmaceutical composition of clause 24, wherein the composition is formulated as a topical composition.

28. The pharmaceutical composition of clause 24, wherein the composition is incorporated into a formulation selected from the group consisting of: cream, lotion, gel, oil, and ointment.

29. The pharmaceutical composition of clause 24, wherein the composition is in a 60 gram, 90 gram, or 120 gram quantity.

30. The pharmaceutical composition of clause 24, wherein the composition is formulated in up to a 4 gram dose.

31. The pharmaceutical composition of clause 24, wherein the composition is formulated in a pharmaceutically acceptable carrier.

32. The pharmaceutical composition of clause 31, wherein the pharmaceutically acceptable carrier is present in an amount of about 55% to about 65%.

33. The pharmaceutical composition of clause 24, wherein nifedipine is present in an amount of about 10%.

34. The pharmaceutical composition of clause 24, wherein pentoxifylline is present in an amount of about 5%.

35. The pharmaceutical composition of clause 24, wherein ketamine hydrochloride is present in an amount of about 10%.

36. The pharmaceutical composition of clause 24, wherein gabapentin is present in an amount of about 6%.

37. The pharmaceutical composition of clause 24, wherein the lidocaine is lidocaine hydrochloride monohydrate and is present in an amount of about 3.7%.

38. The pharmaceutical composition of clause 24, wherein the prilocaine is prilocaine hydrochloride and is present in an amount of about 3.5%.

39. The pharmaceutical composition of clause 24 wherein:
   a) nifedipine is present in an amount of about 10%;
   b) pentoxifylline is present in an amount of about 5%;
   c) ketamine hydrochloride is present in an amount of about 10%;
   d) gabapentin is present in an amount of about 6%;
   e) the lidocaine is lidocaine hydrochloride monohydrate and is present in an amount of about 3.7%; and
   f) the prilocaine is prilocaine hydrochloride and is present in an amount of about 3.5%.

40. The pharmaceutical composition of clause 39, wherein the composition does not contain clonidine.

41. The pharmaceutical composition of clause 39, wherein the composition is formulated as a topical composition.

42. The pharmaceutical composition of clause 39, wherein the composition is incorporated into a formulation selected from the group consisting of: cream, lotion, gel, oil, and ointment.

43. The pharmaceutical composition of clause 39, wherein the composition is in a 60 gram, 90 gram, or 120 gram quantity.

44. The pharmaceutical composition of clause 39, wherein the composition is formulated in up to a 4 gram dose.

45. The pharmaceutical composition of clause 39, wherein the composition is formulated in a pharmaceutically acceptable carrier.

46. The pharmaceutical composition of clause 45, wherein the pharmaceutically acceptable carrier is present in an amount of about 55% to about 65%.

47. A pharmaceutical composition consisting essentially of nifedipine, pentoxifylline, ketamine hydrochloride, gabapentin, lidocaine or a pharmaceutically acceptable salt thereof, prilocaine or a pharmaceutically acceptable salt thereof, and a pharmaceutically acceptable carrier.

48. The pharmaceutical composition of clause 47, wherein the composition is formulated as a topical composition.

49. The pharmaceutical composition of clause 47, wherein the composition is incorporated into a formulation selected from the group consisting of: cream, lotion, gel, oil, and ointment.

50. The pharmaceutical composition of clause 47 wherein:
   a) nifedipine is present in an amount of about 1% to about 25%;
   b) pentoxifylline is present in an amount of about 1% to about 25%;
   c) ketamine hydrochloride is present in an amount of about 10% to about 50%;
   d) gabapentin is present in an amount of about 1% to about 30%;
   e) lidocaine or a pharmaceutically acceptable salt thereof is present in an amount of about 0.1% to about 5%;
   f) prilocaine or a pharmaceutically acceptable salt thereof is present in an amount of about 0.1% to about 5%; and
   g) the pharmaceutically acceptable carrier is present in an amount of about 55% to about 65%.

51. The pharmaceutical composition of clause 50, wherein the composition is formulated as a topical composition.

52. The pharmaceutical composition of clause 50, wherein the composition is incorporated into a formulation selected from the group consisting of: cream, lotion, gel, oil, and ointment.

53. The pharmaceutical composition of clause 50, wherein the composition is in a 60 gram, 90 gram, or 120 gram quantity.

54. The pharmaceutical composition of clause 50, wherein the composition is formulated in up to a 4 gram dose.

55. The pharmaceutical composition of clause 50, wherein nifedipine is present in an amount of about 10%.

56. The pharmaceutical composition of clause 50, wherein pentoxifylline is present in an amount of about 5%.

57. The pharmaceutical composition of clause 50, wherein ketamine hydrochloride is present in an amount of about 10%.

58. The pharmaceutical composition of clause 50, wherein gabapentin is present in an amount of about 6%.

59. The pharmaceutical composition of clause 50, wherein the lidocaine is lidocaine hydrochloride monohydrate and is present in an amount of about 3.7%.

60. The pharmaceutical composition of clause 50, wherein the prilocaine is prilocaine hydrochloride and is present in an amount of about 3.5%.

61. The pharmaceutical composition of clause 50, wherein the pharmaceutically acceptable carrier is present in an amount of about 60.7%.

62. The pharmaceutical composition of clause 50 wherein:
 a) nifedipine is present in an amount of about 10%;
 b) pentoxifylline is present in an amount of about 5%;
 c) ketamine hydrochloride is present in an amount of about 10%;
 d) gabapentin is present in an amount of about 6%;
 e) lidocaine is lidocaine hydrochloride monohydrate and is present in an amount of about 3.7%;
 f) prilocaine is prilocaine hydrochloride and is present in an amount of about 3.5%; and
 g) the pharmaceutically acceptable carrier is present in an amount of about 60.7%.

63. The pharmaceutical composition of clause 62, wherein the composition is formulated as a topical composition.

64. The pharmaceutical composition of clause 62, wherein the composition is incorporated into a formulation selected from the group consisting of: cream, lotion, gel, oil, and ointment.

65. The pharmaceutical composition of clause 62, wherein the composition is in a 60 gram, 90 gram, or 120 gram quantity.

66. A pharmaceutical composition consisting of:
 a) nifedipine in an amount of about 10%;
 b) pentoxifylline in an amount of about 5%;
 c) ketamine hydrochloride in an amount of about 10%;
 d) gabapentin in an amount of about 6%;
 e) lidocaine hydrochloride monohydrate in an amount of about 3.7%;
 f) prilocaine hydrochloride in an amount of about 3.5%;
 g) vitamin E acetate in an amount of about 1%;
 h) sodium metabisulfite in an amount of about 0.5%;
 i) butylated hydroxytoluene in an amount of about 0.05%; and
 j) a pharmaceutically acceptable carrier in an amount of about 60.7%.

67. The pharmaceutical composition of clause 66, wherein the composition is formulated as a topical composition.

68. The pharmaceutical composition of clause 66, wherein the composition is incorporated into a formulation selected from the group consisting of: cream, lotion, gel, oil, and ointment.

69. The pharmaceutical composition of clause 66, wherein the composition is in a 60 gram, 90 gram, or 120 gram quantity.

70. The pharmaceutical composition of clause 66, wherein the composition is formulated in up to a 4 gram dose.

71. A method of treating peripheral neuropathy comprising administering to a patient in need thereof a pharmaceutical composition comprising:
 a) nifedipine in an amount of about 1% to about 25%;
 b) pentoxifylline in an amount of about 1% to about 25%;
 c) ketamine hydrochloride in an amount of about 5% to about 50%;
 d) gabapentin in an amount of about 1% to about 30%;
 e) lidocaine or a pharmaceutically acceptable salt thereof in an amount of about 0.1% to about 5%, and
 f) prilocaine or a pharmaceutically acceptable salt thereof in an amount of about 0.1% to about 5%.

72. The method of clause 71 wherein the peripheral neuropathy is selected from the group consisting of diabetic neuropathy, non-diabetic neuropathy, HIV associated neuropathy, $B_{12}$-deficiency associated neuropathy, cranial nerve palsies, drug-induced neuropathy, industrial neuropathy; lymphomatous neuropathy; myelomatous neuropathy; multi-focal motor neuropathy, chronic idiopathic sensory neuropathy, carcinomatous neuropathy, acute pan autonomic neuropathy, alcoholic neuropathy, compressive neuropathy, and vasculitic/ischaemic neuropathy.

73. The method of clause 71 wherein the peripheral neuropathy is caused by an infectious disease, a post-surgical complication, a toxic agent, low back pain, Guillain-Barre Syndrome, or sciatica.

74. The method of clause 71 wherein the pharmaceutical composition is administered in up to a 4 gram dose.

75. The method of clause 71 further comprising applying heat to a treatment area a first time, applying the pharmaceutical composition to the treatment area, and applying heat to the treatment area a second time.

76. The method of clause 75 further comprising removing excess pharmaceutical composition after applying heat to the treatment area a second time.

77. The method of clause 71 wherein the pharmaceutical composition is administered three times a day.

78. The method of clause 74 wherein the pharmaceutical composition is administered in a 4 gram dose, wherein the 4 gram dose comprises:
 a) 0.4 grams nifedipine;
 b) 0.2 grams pentoxifylline;
 c) 0.4 grams ketamine hydrochloride;
 d) 0.24 grams gabapentin;
 e) 0.15 grams lidocaine hydrochloride monohydrate;
 f) 0.14 grams prilocaine hydrochloride;
 g) 0.04 grams vitamin E acetate;
 h) 0.002 grams sodium metabisulfite;
 i) 0.002 grams butylated hydroxytoluene; and
 j) 2.43 grams Lipoderm® ActiveMax base.

EXAMPLES

Preparation of a Bulk Composition (60 g)

In a compounding vessel equipped with a mixer nifedipine (6 g), pentoxifylline (3 g), ketamine hydrochloride (6 g), gabapentin (3.6 g), lidocaine hydrochloride monohydrate (2.2 g), prilocaine hydrochloride (2.1 g), vitamin E acetate (0.6 g), sodium metabisulfite (0.03 g) butylated hydroxytoluene (0.03 g), and Lipoderm ActiveMax (36.4 g) were combined and mixed. The composition was then milled in an Exakt 120S-450 Three Roll Mill (front roll "1", rear roller "3"). The composition was then stirred and packaged.

The present invention may be embodied in other forms without departing from the spirit or essential attributes thereof and, accordingly, reference should be had to the following claims rather than the foregoing specification as indicating the scope of the invention. Further, the illustrations of arrangements described herein are intended to provide a general understanding of the various embodiments, and they are not intended to serve as a complete description. Many other arrangements will be apparent to those of skill in the art upon reviewing the above description. Other arrangements may be utilized and derived therefrom, such that logical substitutions and changes may be made without departing from the scope of this disclosure.

This disclosure is intended to cover any and all adaptations or variations of various embodiments and arrangements of the invention. Combinations of the above arrangements, and other arrangements not specifically described herein, will be apparent to those of skill in the art upon reviewing the above description. Therefore, it is intended that the disclosure not be limited to the particular arrangement(s) disclosed as the best mode contemplated for carrying out this invention, but that the invention will include all embodiments and arrangements falling within the scope of the appended claims.

What is claimed is:

1. A pharmaceutical composition consisting of nifedipine, pentoxifylline, ketamine hydrochloride, gabapentin, lidocaine or a pharmaceutically acceptable salt thereof, prilocaine or a pharmaceutically acceptable salt thereof, and a pharmaceutically acceptable carrier.

2. The pharmaceutical composition of claim 1, wherein the composition is formulated as a topical composition.

3. The pharmaceutical composition of claim 1, wherein the composition is incorporated into a formulation selected from the group consisting of: cream, lotion, gel, oil, and ointment.

4. The pharmaceutical composition of claim 1 wherein:
   a) nifedipine is present in an amount of about 1% to about 25%;
   b) pentoxifylline is present in an amount of about 1% to about 25%;
   c) ketamine hydrochloride is present in an amount of about 10% to about 50%;
   d) gabapentin is present in an amount of about 1% to about 30%;
   e) lidocaine or a pharmaceutically acceptable salt thereof is present in an amount of about 0.1% to about 5%;
   f) prilocaine or a pharmaceutically acceptable salt thereof is present in an amount of about 0.1% to about 5%; and
   g) the pharmaceutically acceptable carrier is present in an amount of about 55% to about 65%.

5. The pharmaceutical composition of claim 4, wherein the composition is formulated as a topical composition.

6. The pharmaceutical composition of claim 4, wherein the composition is incorporated into a formulation selected from the group consisting of: cream, lotion, gel, oil, and ointment.

7. The pharmaceutical composition of claim 4, wherein the composition is in a 60 gram, 90 gram, or 120 gram quantity.

8. The pharmaceutical composition of claim 4, wherein the composition is formulated in up to a 4 gram dose.

9. The pharmaceutical composition of claim 4, wherein nifedipine is present in an amount of about 10%.

10. The pharmaceutical composition of claim 4, wherein pentoxifylline is present in an amount of about 5%.

11. The pharmaceutical composition of claim 4, wherein ketamine hydrochloride is present in an amount of about 10%.

12. The pharmaceutical composition of claim 4, wherein gabapentin is present in an amount of about 6%.

13. The pharmaceutical composition of claim 4, wherein the lidocaine is lidocaine hydrochloride monohydrate and is present in an amount of about 3.7%.

14. The pharmaceutical composition of claim 4, wherein the prilocaine is prilocaine hydrochloride and is present in an amount of about 3.5%.

15. The pharmaceutical composition of claim 4, wherein the pharmaceutically acceptable carrier is present in an amount of about 60.7%.

16. The pharmaceutical composition of claim 4 wherein:
   a) nifedipine is present in an amount of about 10%;
   b) pentoxifylline is present in an amount of about 5%;
   c) ketamine hydrochloride is present in an amount of about 10%;
   d) gabapentin is present in an amount of about 6%;
   e) lidocaine is lidocaine hydrochloride monohydrate and is present in an amount of about 3.7%;
   f) prilocaine is prilocaine hydrochloride and is present in an amount of about 3.5%; and
   g) the pharmaceutically acceptable carrier is present in an amount of about 60.7%.

17. The pharmaceutical composition of claim 16, wherein the composition is formulated as a topical composition.

18. The pharmaceutical composition of claim 16, wherein the composition is incorporated into a formulation selected from the group consisting of: cream, lotion, gel, oil, and ointment.

19. The pharmaceutical composition of claim 16, wherein the composition is in a 60 gram, 90 gram, or 120 gram quantity.

20. A pharmaceutical composition consisting of:
   a) nifedipine in an amount of about 10%;
   b) pentoxifylline in an amount of about 5%;
   c) ketamine hydrochloride in an amount of about 10%;
   d) gabapentin in an amount of about 6%;
   e) lidocaine hydrochloride monohydrate in an amount of about 3.7%;
   f) prilocaine hydrochloride in an amount of about 3.5%;
   g) vitamin E acetate in an amount of about 1%;
   h) sodium metabisulfite in an amount of about 0.5%;
   i) butylated hydroxytoluene in an amount of about 0.05%; and
   j) a pharmaceutically acceptable carrier in an amount of about 60.7%.

21. The pharmaceutical composition of claim 20, wherein the composition is formulated as a topical composition.

22. The pharmaceutical composition of claim 20, wherein the composition is incorporated into a formulation selected from the group consisting of: cream, lotion, gel, oil, and ointment.

23. The pharmaceutical composition of claim 20, wherein the composition is in a 60 gram, 90 gram, or 120 gram quantity.

24. The pharmaceutical composition of claim 20, wherein the composition is formulated in up to a 4 gram dose.

* * * * *